US010736326B2

(12) United States Patent
Kaplan

(10) Patent No.: US 10,736,326 B2
(45) Date of Patent: Aug. 11, 2020

(54) NEMATODE DISPERSANT COMPOSITION AND METHOD

(71) Applicant: PHERONYM, INC., Gainesville, FL (US)

(72) Inventor: Fatma Kaplan, Gainesville, FL (US)

(73) Assignee: PHERONYM, INC., Gainesville, FL (US)

( * ) Notice: Subject to any disclaimer, the term of this patent is extended or adjusted under 35 U.S.C. 154(b) by 0 days.

(21) Appl. No.: 15/777,907

(22) PCT Filed: Jan. 4, 2017

(86) PCT No.: PCT/US2017/012208

§ 371 (c)(1),
(2) Date: May 21, 2018

(87) PCT Pub. No.: WO2017/120252

PCT Pub. Date: Jul. 13, 2017

(65) Prior Publication Data

US 2018/0343873 A1 Dec. 6, 2018

Related U.S. Application Data

(60) Provisional application No. 62/274,843, filed on Jan. 5, 2016.

(51) Int. Cl.

| | |
|---|---|
| ***A01N 63/02*** | (2006.01) |
| ***A01N 25/04*** | (2006.01) |
| ***C12N 5/07*** | (2010.01) |
| ***A01N 63/10*** | (2020.01) |

(52) U.S. Cl.

CPC ............ *A01N 63/10* (2020.01); *A01N 25/04* (2013.01); *C12N 5/0601* (2013.01); *C12N 2500/30* (2013.01); *C12N 2500/70* (2013.01); *C12N 2523/00* (2013.01); *C12N 2527/00* (2013.01)

(58) Field of Classification Search

CPC ........... A01N 63/02; A01N 25/04; C12N 5/07
See application file for complete search history.

(56) References Cited

U.S. PATENT DOCUMENTS

2014/0364386 A1* 12/2014 Choe .................. A61K 31/454
514/32

* cited by examiner

*Primary Examiner* — Zohreh A Fay
(74) *Attorney, Agent, or Firm* — Gerard H. Bencen

(57) ABSTRACT

Nematode dispersal is one of the key features for success as a biocontrol agent. Currently, commercially available nematodes do not disperse sufficiently when they are applied to a field. Since the insect target is mobile, nematodes need to be actively moving and seeking an insect host. We developed a pheromone extract from nematode growth medium that disperses nematodes. This extract was unstable in liquid form. We have found that the extract can be dried to retain activity during storage or shipment. Exposing nematodes to pheromone extract before they are applied to a field activates them to disperse and seek a new host. This exposure needs to be at least 20 min. When nematodes are actively seeking a new host this increases nematode insect encounter and increases insect mortality leading to increased effectiveness of insect nematodes as biological control agents.

11 Claims, 5 Drawing Sheets

NEMATODE DISPERSANT COMPOSITION AND METHOD

1.0 FIELD OF THE INVENTION

Methods and compositions to induce dispersal of insect nematodes.

2.0 BACKGROUND OF THE INVENTION

Nematode dispersal is one of the key features for success as a biocontrol agent to control insects which destroy commercially valuable crops. Currently, commercially available nematodes do not disperse sufficiently when they are applied to a field, leaving clumps of nematodes which cannot properly find and parasitize plant destructive insects. Since the insect target is mobile, nematodes need to be actively moving and seeking insect hosts.

Figure 1:
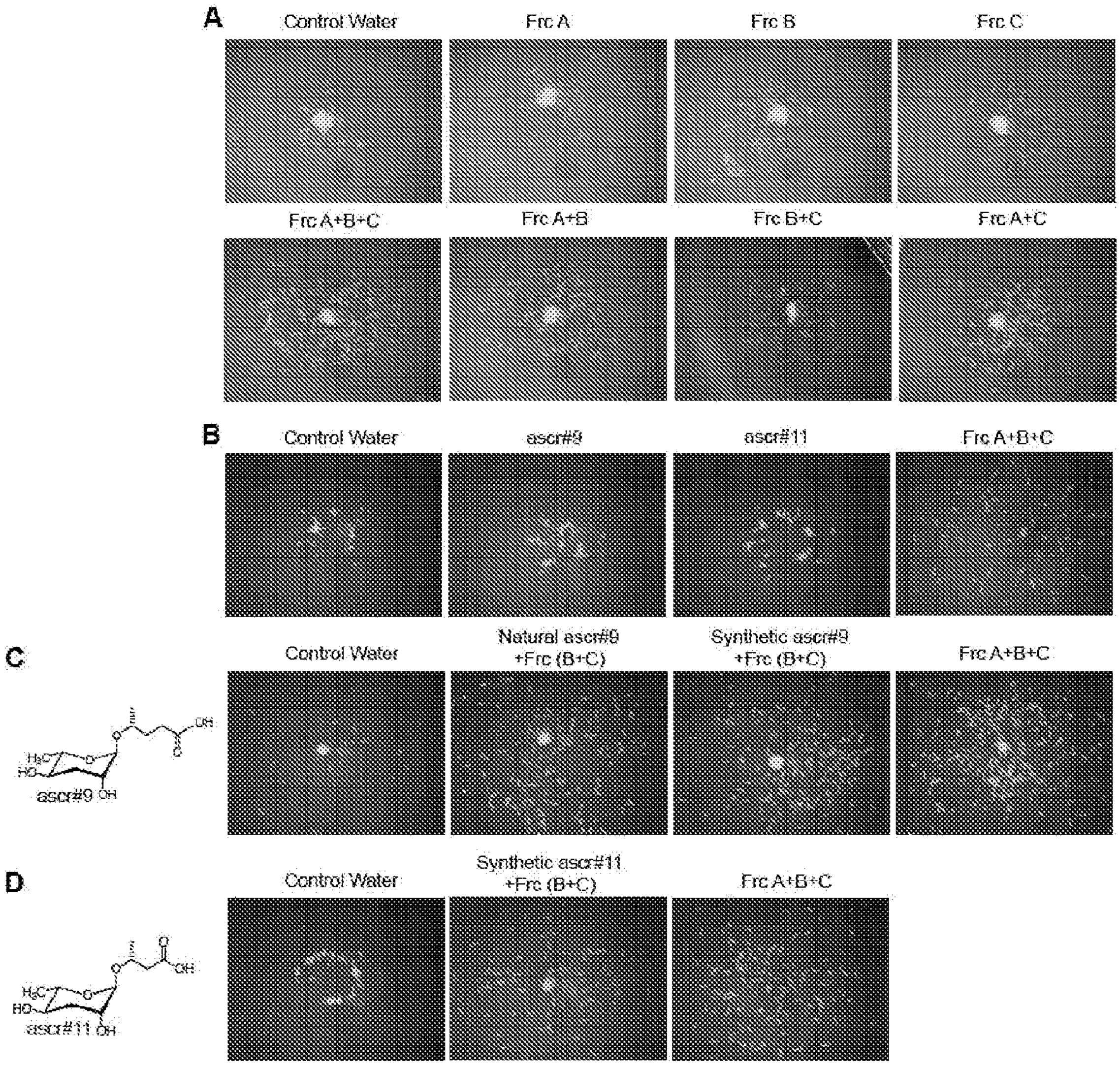

While it has been proposed that dispersal of insect nematode infective juveniles (IJs) is regulated by ascaroside pheromones (Kaplan et al 2012, Choe at el 2012), as shown herein, it is a blend of pheromones that regulate this behavior (FIG. 1). Only one component of this blend is known and that component by itself is insufficient to disperse nematodes (entomopathogenic nematodes, EPNs). As shown herein, a pheromone blend (FIG. 2) disperses *Caenorhabditis elegans*, a model nematode, which is also recognized by insect nematodes. However, *C. elegans* synthetic pheromone blend does not disperse insect nematodes as well as insect nematode pheromone extracts. We disclose herein compositions, methods of making such compositions and methods of using the compositions to optimally induce nematode dispersal activity.

3.0 SUMMARY OF THE INVENTION

This patent disclosure provides a dried nematode growth medium extract to treat insect nematodes prior to field application for improved dispersal and field efficacy, including a pheromone extract of nematode growth medium which induces dispersal of insect nematodes for improved nematode field efficacy. Methods of manufacture, including purification, storage as dry powder, and use are disclosed for optimal preservation and use of the nematode dispersal activity.

The dispersal behavior of nematodes disclosed herein is surprisingly controlled by pheromones. It is not obvious that dispersal pheromones are found in nematode growth medium. Since dispersal activity is labile, prior to this patent disclosure, it was not known how to obtain the dispersal signal, how to preserve the activity, or how to deploy the activity to commercial advantage.

Treatment with crude pheromone induces dispersal in insect nematodes, which improves the potential for encounters with insect hosts and insect mortality. The pheromone composition disclosed and claimed herein was partially purified from nematode growth medium, including but not limited to, insects, liquid broth, or agar plates. The pheromones were extracted using an alcohol, such as but not limited to, 70% methyl alcohol, ethyl alcohol, or combinations thereof, and centrifugation to remove insoluble debris (see FIG. 4). The pheromone can be extracted with a range of concentration from about 10% to about 95% alcohol. The liquid (supernatant) was removed and concentrated to produce a dry extract by using a stream of nitrogen, by lyophilization, or by equivalent means. The dry powder was resuspended in water and centrifuged to separate insoluble debris from water-soluble pheromones. The supernatant was concentrated to dryness using a lyophilizer or equivalent means for storage. In liquid storage, the activity was lost within 3 weeks at −20° C. and at a faster rate at ambient temperatures. We have discovered, however, that drying the extract preserves the activity of the water-soluble partially purified pheromone blend. The ratio of this pheromone mixture was important for the activity. When the extract was diluted up to 3 times it produced dispersal activity, but the activity was diminished upon further dilution. For example, 1 insect host extract from *Galleria mellonella* (average weight of *G. mellonella* larvae, wax worm, is estimated to be 200 microL (microliters) or 232+/−57 mg) is diluted in 200 microL water up to 600 microL water. A commercial package of 5 million insect nematodes would require production of an extract from about 200 *G. mellonella* diluted to between about 40 ml and 120 ml. The extracts are not limited to *G. mellonella*. Insect host preinfected weight is considered 1:1 for extract dilution and up to 3 times of the original weight of the extract is active. For the liquid broth, a 1 L (liter) growth medium where the food (as bacteria) density goes down and nematode density goes up and the IJs or analogous life stage (e.g. dauer in *C. elegans*) forms, the media contains dispersal pheromone. One L liquid broth extract (dry powder) is diluted with 1 L water up to 3 L of water. A package of commercial insect nematodes (5 million nematodes) is preferably exposed to about 100 ml of the extract from liquid growth medium. The powder is resuspended with nematodes to activate the nematodes for dispersal before spraying the nematodes in a field (see FIG. 5). According to one embodiment of the invention, nematodes are treated with resuspended powder for at least about 15-30 min (minute), and most preferably for about 20 min, prior to field applications. In alternate embodiments, the resuspended extract is mixed with nematodes as the nematodes are applied to the field.

The most potent nematode dispersant we have tested was partially purified pheromone extract (FIG. 3) from nematode growth medium (liquid broth or insect host cadavers).

The partial purification methods (FIG. 4) include a drying stage for storage. We have found that the dispersal inducing activity is rapidly lost in aqueous solution. However, drying the extracts preserves the activity. Therefore, partially purified pheromone extract is one composition according to this invention which is dried to preserve the dispersal activity.

4.0 BRIEF DESCRIPTION OF THE DRAWINGS

FIG. 1: Activity guided fractionation of the *S. feltiae* dispersal pheromone. (A) Reverse phase (C18) chromatography of insect cadaver extract. The image represents two independent experiments. The estimated physiologically relevant concentration was used in the assays; Frc, fraction. (B) Testing physiologically relevant concentration of ascarosides found in Frc A (ascr#9, 40.3 pmol/μl and ascr#11, 1.3 pmol/μl). Image represents three experiments. (C) Structure of ascr#9. Natural and synthetic ascr#9 were tested in combination with fraction B and C. Image represents four experiments. (D) Structure of ascr#11. It (1.3 pmol/μl) is also sufficient to cause dispersal in combination with fractions B and C. Image represents three experiments.

Figure 2:
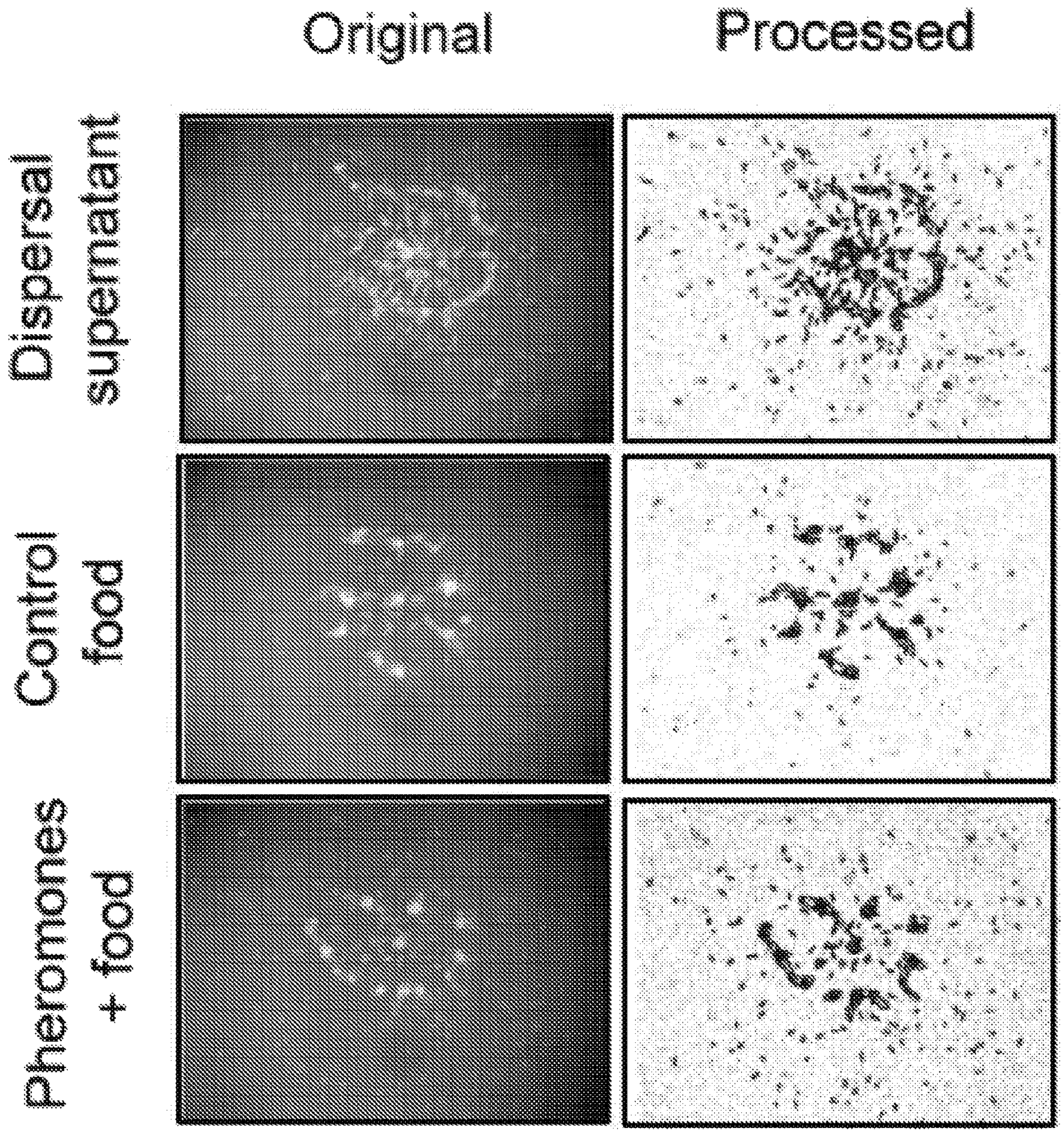

FIG. 2: An ascaroside pheromone blend regulates *C. elegans* dispersal behavior. Left panel: Identification of the dispersal blend. Images (250 nematodes) are representative of 9, 10, and 11 experiments of control (0.25% *E. coli* (HB101)), synthetic blend with 0.25% *E. coli* (HB101) and pheromone extract of liquid broth, respectively. Right panel processed image using ImageJ (http://rsbweb.nih.gov/ij/download.html) to show the difference between pheromone extract and synthetic pheromone blend.

Figure 3:
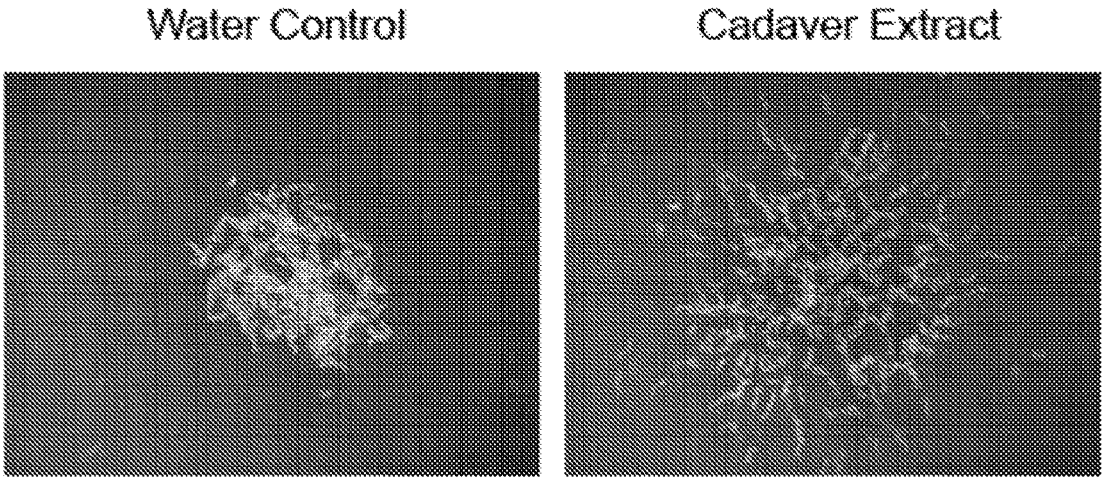

FIG. 3: Dispersal assay *S. feltiae* infective juveniles (IJ). Approximately 300 IJs were placed on an agar plate in water. IJs were treated with either water (control) or insect cadaver extract. Images are representative of six experiments for each treatment.

Figure 4:
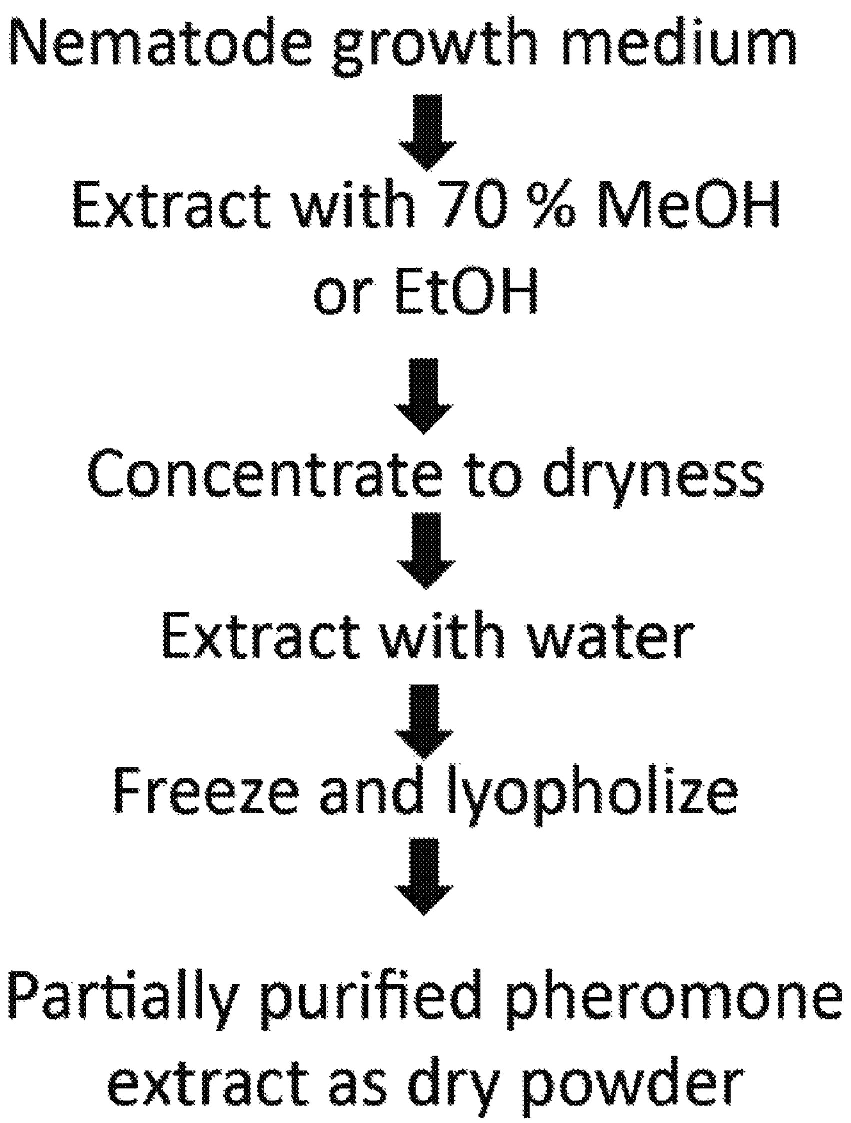

FIG. 4: Purification procedure of pheromone extract from nematode growth medium.

Figure 5:
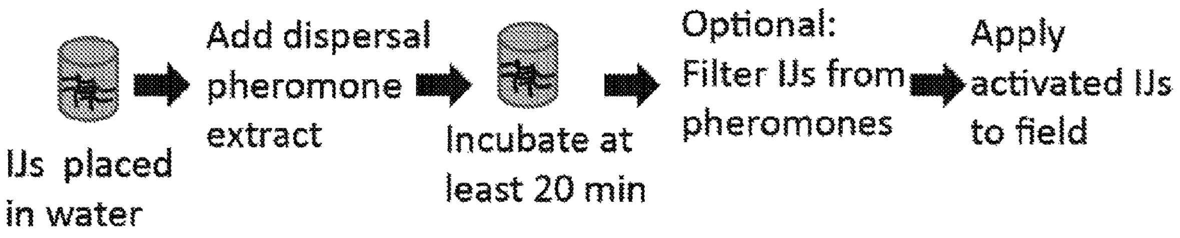

FIG. 5: Application of partially purified extract to IJs before field application.

5.0 DETAILED DISCLOSURE OF THE PREFERRED EMBODIMENTS OF THE INVENTION

Methods of making and using the nematode dispersal composition according to this invention are described in detail herein below and are supported by the Examples provided herein.

FIG. 1 A shows that dispersal behavior is regulated by a chemical based on the fractionation of crude extract and that a blend of compounds is required. FIG. 1B shows two of the ascaroside pheromones (ascr#9 and ascr#11) were found in Fraction A. Consistent with FIG. 1A, these ascaroside pheromones are not active by themselves. FIG. 1C shows that natural ascr#9 is active with fraction B and C. Use of synthetic ascr#9 with fraction B and C also confirms the active component of fraction A that is an ascaroside pheromone and is not active by itself. FIG. 1D shows ascr#11 is a structural analog of ascr#9 and is expected to be sufficient to give activity with Fraction B and C. It is active with the other two fractions, but not by itself.

The dispersal behavior is regulated by pheromones in other nematode species (FIG. 2). The *C. elegans* dauer stage, which is analogous to the infectious juvenile or "IJ" stage in insect nematodes, is tested for dispersal assays (Kaplan et al 2012). The left panel shows dispersal supernatant which gives full dispersal activity, then control with food and pheromone blend with food. Pheromones disperse nematodes from perfectly good food. The right panel shows the ImageJ processed figure which shows the difference better. The original extract disperses the nematodes better than the identified pheromone blend.

In insect nematodes, the partially purified pheromone extract from insect cadavers disperses IJs of the insect nematode *S. feltiae* (FIG. 3). Even though *S. feltiae* recognizes (Kaplan et al 2012) *C. elegans* dispersal pheromone blend, the partially purified extract from its own growth medium still works better.

Purification procedure (FIG. 4): In a preferred embodiment, a ratio of alcohol (EtOH or MeOH) per insect host cadaver was 1:1 (1 ml of 70% EtOH or MeOH per insect cadaver; the effective concentration range was 10% to 95% alcohol). If the ratio was not 1:1, the dispersal activity was less efficiently extracted. The insect cadavers were homogenized. Samples were centrifuged and the supernatant was concentrated to dryness via lyophilization or equivalent means. Then samples were extracted with water and centrifuged to separate insoluble compounds. The supernatant was frozen and dried by lyophilization or equivalent means. The dry powder was stored either at ambient temperature or in a freezer.

In the laboratory experiments, when the extract is added to the nematode suspension on an agar plate, it took 15 to 20 min for the water to be absorbed by the medium where the nematodes became free. Since the nematodes are deconditioned to pheromone, just adding water did not activate them. Only the pheromone extract activated them. Based on laboratory plate assays we estimate they need at least about 5-30 min pheromone exposure. This could be as little as 5 min or as much as 30 min, and most preferably is about 20 min.

Dry powder is added to commercially available nematode water suspension (FIG. 5) and incubated for about 20 min to activate the IJs. Once the IJs are activated, optionally after they can be filtered to remove the dispersal pheromone, they are applied to a field with commercially available apparatus.

Non-limiting description of nematodes and hosts to which the present invention is applicable include the following:

Commercially available nematodes: Insect nematodes, entomopathogenic nematodes, in the genera *Heterorhabditis* and *Steinernema* species such as *Steinernema carpocapsae, Steinernema feltiae, Steinernema kraussei, Steinernema glaseri, Steinernema scapterisci, Steinernema riobrave, Steinernema kushidai, Steinernema scarabaei* or *Heterorhabditis bacteriophora, Heterorhabditis megidis, Heterorhabditis indica, Heterorhabditis marelatus, Heterorhabditis zealandica, Heterorhabditis downesi, Heterorhabditis marelata, Heterorhabditis marelatus.*

Insects that are controlled by nematodes: Artichoke plume moth, Armyworms, Banana moth, Banana root borer, Billbug, Black cutworm, Black vine weevil, Borers, Cat flea, Chinch bugs, Citrus root weevil, Codling moth, Corn earworm, Corn rootworm, Cranberry girdler, Crane fly, Diaprepes root weevil, Fungus gnats, Grape root borer, Iris borer, Large pine weevil, Leafminers, Mole crickets, Navel orangeworm, Plum curculio, Scarab grubs, Shore flies, Strawberry root weevil, Small hive beetle, Sod webworms Sweetpotato weevil.

For example: *S. carpocapsae* controls insect pests such as cutworms, armyworms, billbugs, cranberry girdler, peach tree borer, fleas, chinch bug, black vine weevil, strawberry root weevil, webworm and artichoke plume moth.

*S. feltiae* is sold widely for control of *thrips*, fungus gnats, codling moth, larvae of vine weevils and sciarids.

*S. kraussei* seek out suitable hosts by swimming in the thin film of water on soil particles.

*H. bacteriophora* controls *Otiorhyncus sulcatus*, Black Vine Weevil, larvae feeding on roots in the soil and chafer grubs.

Commercial use of entomopathogenic nematodes (EPN) *Steinernema* and *Heterorhabditis* as bioinsecticides.

| EPN species | Major pest(s) targeted—as recommended by various commercial companies |
|---|---|
| *Steinernema glaseri* | White grubs (scarabs, especially Japanese beetle, *Popillia* sp.), banana root borers |
| *Steinernema kraussei* | Black vine weevil, *Otiorhynchus sulcatus* |
| *Steinernema carpocapsae* | Turfgrass pests—billbugs, cutworms, armyworms, sod webworms, chinch bugs, crane flies. Orchard, ornamental and vegetable pests—banana moths, codling moths, cranberry girdlers, dogwood borers and other clearwing borer species, black vine weevils, peachtree borers, shore flies (*Scatella* spp.) |
| *Steinernema feltiae* | Fungus gnats (*Bradysia* spp.), shore flies, western flower thrips, leafminers |
| *Steinernema scapterisci* | Mole crickets (*Scapteriscus* spp.) |
| *Steinernema riobrave* | Citrus root weevils (*Diaprepes* spp.), |

-continued

| EPN species | Major pest(s) targeted—as recommended by various commercial companies |
|---|---|
| | mole crickets |
| *Heterorhabditis bacteriophora* | White grubs (scarabs), cutworms, black vine weevils, flea beetles, corn root worms, citrus root weevils |
| *Heterorhabditis megidis* | Weevils |
| *Heterorhabditis indica* | Fungus gnats, root mealybugs, grubs |
| *Heterorhabditis marelatus* | White grubs (scarabs), cutworms, black vine weevils |
| *Heterorhabditis zealandica* | Scarab grubs |

See: http://entnemdept.ufl.edu/creatures/nematode/entomopathogenic_nematode.htm

Nematodes species used are abbreviated as follows: Hb=*Heterorhabditis bacteriophora*, Hd=*H. downesi*, Hi=*H. indica*, Hm=*H. marelata*, Hmeg=*H. megidis*, Hz=*H. zealandica*, Sc=*Steinernema carpocapsae*, Sf=*S. feltiae*, Sg=*S. glaseri*, Sk=*S. kushidai*, Sr=*S. riobrave*, Sscap=*S. scapterisci*, Ss=*S. scarabaei*.

| Pest Common name | Pest Scientific name | Key Crop(s) targeted | Efficacious Nematodes * |
|---|---|---|---|
| Artichoke plume moth | *Platyptilia carduidactyla* | Artichoke | Sc |
| Armyworms | Lepidoptera: Noctuidae | Vegetables | Sc, Sf, Sr |
| Banana moth | *Opogona sachari* | Ornamentals | Hb, Sc |
| Banana root borer | *Cosmopolites sordidus* | Banana | Sc, Sf, Sg |
| Billbug | *Sphenophorus* spp. (Coleoptera: Curculionidae) | Turf | Hb, Sc |
| Black cutworm | *Agrotis ipsilon* | Turf, vegetables | Sc |
| Black vine weevil | *Otiorhynchus sulcatus* | Berries, ornamentals | Hb, Hd, Hm, Hmeg, Sc, Sg |
| Borers | *Synanthedon* spp. and other sesiids | Fruit trees & ornamentals | Hb, Sc, Sf |
| Cat flea | *Ctenocephalides felis* | Home yard, turf | Sc |
| Citrus root weevil | *Pachnaeus* spp. (Coleoptera: Curculionidae | Citrus, ornamentals | Sr, Hb |
| Codling moth | *Cydia pomonella* | Pome fruit | Sc, Sf |
| Corn earworm | *Helicoverpa zea* | Vegetables | Sc, Sf, Sr |
| Corn rootworm | *Diabrotica* spp. | Vegetables | Hb, Sc |
| Cranberry girdler | *Chrysoteuchia* topiaria | Cranberries | Sc |
| Crane fly | Diptera: Tipulidae | Turf | Sc |
| Diaprepes root weevil | *Diaprepes abbreviatus* | Citrus, ornamentals | Hb, Sr |
| Fungus gnats | Diptera: Sciaridae | Mushrooms, greenhouse | Sf, Hb |
| Grape root borer | *Vitacea polistiformis* | Grapes | Hz, Hb |
| Iris borer | *Macronoctua onusta* | Iris | Hb, Sc |
| Large pine weevil | *Hyloblus albietis* | Forest plantings | Hd, Sc |
| Leafminers | *Liriomyza* spp. (Diptera: Agromyzidae) | Vegetables, ornamentals | Sc, Sf |
| Mole crickets | *Scapteriscus* spp. | Turf | Sc, Sr, Scap |
| Navel orangeworm | *Amyelois transitella* | Nut and fruit trees | Sc |
| Plum curculio | *Conotrachelus nenuphar* | Fruit trees | Sr |
| Scarab grubs** | Coleoptera: Scarabaeidae | Turf, ornamentals | Hb, Sc, Sg, Ss, Hz |
| Shore flies | *Scatella* spp. | Ornamentals | Sc, Sf |
| Strawberry root weevil | *Otiorhynchus ovatus* | Berries | Hm |
| Small hive | *Aethina tumida* | Bee hives | Yes (Hi, Sr) |

-continued

| Pest Common name | Pest Scientific name | Key Crop(s) targeted | Efficacious Nematodes * |
|---|---|---|---|
| beetle | | | |
| Sweetpotato weevil | *Cylas formicarius* | Sweet potato | Hb, Sc, Sf |

See: http://www.biocontrol.entomology.cornell.edu/pathogens/nematodes.php

In light of the foregoing disclosure, those skilled in the art will appreciate that this invention includes a method for obtaining an entomopathogenic nematode ("EPN") dispersal inducing composition by obtaining a nutrient depleted EPN growth medium selected from liquid broth, agar medium, and insect host cadaver, depleted of nutrients by growing said EPN to stasis in said growth medium. From the growth medium, (e.g. with insect host cadavers, alcohol is added to the cadavers because the volume is very small; with liquid broth, it can be first frozen and then lyophilized because the initial volume is large, and then extracted with alcohol), producing an alcohol-growth medium mixture by adding an alcohol to the growth medium to achieve a final concentration of between about 10% to about 95% of the alcohol in the growth medium. The alcohol-growth medium mixture is centrifuged to remove solid or insoluble matter while maintaining a supernatant from the centrifugation step. Preferably, the supernatant from the centrifuging step is dried to produce a dry extract. The dry extract is then, preferably, resuspended in water or equivalent aqueous medium to produce a water soluble pheromone extract. The water soluble pheromone extract is preferably again centrifuged to remove water/aqueous medium insoluble compounds while maintaining a water soluble supernatant. To preserve the activity, the supernatant from this centrifugation step is dried to produce a dry EPN dispersal composition.

In a preferred embodiment, the alcohol is selected from the ethanol, methanol and mixtures thereof. In another preferred embodiment, the growth medium is selected from a growth medium in which non-pathogenic bacterivore nematodes or insect or entomopathogenic nematodes have been grown.

According to this invention, the dispersal composition is produced by a method as described herein. Furthermore, using activity guided purification, fractions of the composition are produced and combined in differing ratios so as to produce an active mixture.

In a further embodiment according to the invention, the composition according to this invention is used to disperse nematodes in field application of the nematodes by dissolving the composition in an aqueous medium to produce an aqueous EPN dispersal composition. The aqueous EPN dispersal composition is mixed with nematodes to activate the nematodes for dispersal prior to field application of the nematodes. The nematodes, in a preferred embodiment, nematodes are maintained in contact with an aqueous EPN dispersal composition according to this invention for a period of at least about 20 min prior to field application of the nematodes. In a further embodiment, the nematodes are filtered prior to field application.

While different embodiments of the invention are described herein, those skilled in the art will appreciate that permutations and combinations of these embodiments may be utilized to advantage without departing from the invention.

6.0 EXAMPLES

While the foregoing disclosure is considered to provide an adequate written description and enabling disclosure of the invention disclosed and claimed herein, the following examples are provided to ensure that those skilled in the art reading this patent disclosure are put in possession of this invention as of the date of its filing. The specifics of these examples should not, however, be considered as limiting on the scope of the invention as broadly disclosed and claimed herein. Furthermore, those skilled in the art will appreciate that equivalents and modifications of the invention disclosed herein come within the scope of the present claims.

Example 1

Activity Guided Purification of Nematode Dispersal Activity

The dispersal assay for the activity guided purification in FIG. 1 used *S. feltiae* IJs that were washed with MILLI-Q water three times and incubated in 6 cm petri dishes for 36 h with a small amount (4-5 ml) of MILLI-Q water. The following day, nematodes were placed on a 10.7 g/L agar with gel strength 1010 g/cm$^2$ (PhytoTechnology Lab. Shawnee Mission, Kans.). Nematode behavior was assayed on multiple plates with internal plate replicates to rule out the possibility that behavior was affected by plate composition. Approximately 300 IJs in 10 μl water were placed on an agar medium and the test compounds or extracts were placed into 1-2 μl to the nematode suspension. Upon absorption (15-20 min) of the liquid, the freely moving nematodes were video-recorded for 5-10 min. Dispersal behavior is temperature and season dependent. During winter, the assay is effective at RT (22±1° C.). During summer, the assay requires a temperature-controlled environment due to effects on nematode behavior above 23° C.

Activity guided fractionation was conducted as described by Srinivasan et al 2008 with modifications. A total of 33 insect host cadavers (*G. mellonella* larvae) were placed into 70% EtOH and stored at −20° C. until extraction. The insect cadavers were homogenized using 1 g of ceramic zirconium beads (1.25 mm) (ZIRMIL) in 2 ml tubes for 37 sec using a Precellys24 (http://www.precellys.com) homogenizer. Samples were centrifuged for 15 min at 18400 rcf and the supernatant was lyophilized and resuspended in MILLI-Q water. The dispersal activity of nematodes was tested using the dispersal assay described herein above and a physiologically relevant concentration of insect host cadaver extract or fractionated extract. To facilitate calculations for physiologically relevant concentration of the ascarosides, wax worm volume was estimated at 200 μl; the average weight of wax worms was 232 (+/−57 mg; n=19).

The first reverse-phase solid-phase extraction was performed using Sep-Pak Plus C18 cartridges (Waters corporation, Milford, Mass.). The initially collected flow through was termed Fraction A. Thereafter, the column was washed with water, collected and saved. Subsequently, the column was eluted with 50% (Fraction B) and 90% MeOH (Fraction C). The fractions were tested for dispersal activity both individually and in combination. Also individual fractions were analyzed by LC-MS. Fraction A contained ascr#9, which was collected by LC-MS and tested for activity with Fraction B+C.

Comparative metabolomics by itself or in combination with activity guided purification, and/or mass guided purification of ascarosides is used to identify the components of the EPN dispersal inducing composition according to this invention.

Comparative metabolomics have been used in *C. elegans* to identify *C. elegans* dispersal blend (Kaplan et al 2012). Briefly, liquid cultures that induced 60% dauer (2 experiments) and 40% dauer after 67 h of feeding L1s were analyzed using LC-MS. Four ascarosides were common to all three liquid media. The concentrations of each were measured from the liquid cultures that produced 60% dauers.

One of the major components, ascr#9, was found to be common in insect host cadavers of *Steinernema* spp. and *Heterorhabditis* spp. (Kaplan et al 2012). Briefly, insect hosts (*G. mellonella*) were infected with *H. bacteriophora, H. zealandica, H. floridensis, S. carpocapsae, S. riobrave*, or *S. diaprepesi*. When nematodes began to emerge from insect cadavers, they were placed into 1.5 ml of 70% EtOH and stored at −20° C. until use. Thereafter, insect cadavers were homogenized using 1 g of ceramic zirconium beads (1.25 mm) (ZIRMIL) in 2 ml tubes for 39 sec using a Precellys24 homogenizer. The homogenized cadavers were centrifuged at 3380 rcf for 10 min. The supernatant was diluted with 1 ml of HPLC water and placed at −20° C. and then placed into a speed vac (Speed Vac Plus SC210A, Savant) overnight. Each cadaver extract was re-suspended in 1 ml of 50% MeOH and centrifuged at 18400 rcf for 15-20 min. Thereafter, samples were diluted in a 1:1 ratio with 0.1% formic acid, yielding sample pH of 4.2. Presence or absence of ascr#9 was determined by LC-MS.

This suggested that the other components of the dispersal blend can be common in insect host cadavers infected with other *Steinernema* and *Heterorhabditis* species. One species can recognize the others' dispersal blend. Since the dispersal signal tells the nematodes the environment is low food and high density, it is anticipated that many nematodes will recognize this signal.

It has been demonstrated that *S. feltiae* recognizes another bacterivore, *C. elegans*,' dispersal pheromone blend (Kaplan et al 2012).

A total of 33 insect host cadavers (*C. mellonella* larvae) were placed into 70% EtOH and were homogenized using 1 g of ceramic zirconium beads (1.25 mm) (ZIRMIL) in 2 ml tubes for 37 sec using a Precellys24 (http://www.precellys.com) homogenizer. Samples were centrifuged for 15 min at 18400 rcf and the supernatant was lyophilized and resuspended in MILLI-Q water. The dispersal activity of nematodes was tested using the dispersal assay described herein above. The extracts were resuspended in water as 10 times concentrated. The average weight of insect host is estimated 200 microL and therefore the dry cadavers extract from 1 insect equivalent was diluted in 20 microL of water. One microL of the concentrated extracts was added to the 10 ul of IJ water suspension.

Example 2

Dispersal Activity

The dispersal assay for *C. elegans* was adapted from *S. feltiae*. Briefly, *C. elegans* dauer juveniles were washed with MILLI-Q water 3 times and placed into 6 cm petri dishes with a small amount of water and rested overnight. Approximately 200-300 nematodes in 10 μl of water were placed on an agar plate and 2 μl of treatment was added. The liquid culture that produced 60% dauer animals was centrifuged and filtered with a 0.45 μm filter and used as a positive control for dispersal. Thereafter, media were lyophilized and resuspended in MILLI-Q water 5 times and 2 μl to 10 μl of nematode suspension was used for assay. As a negative control, 0.5% *E. coli* (HB101) was prepared in S-complete, lyophilized and adjusted to the final volume of 0.25% *E. coli* in the assay. The dispersal behavior was observed for 12-15 min.

Liquid cultures that induced 60% dauer (2 experiments) and 40% dauer after 67 h of feeding L1s were analyzed using Liquid Chromatography and Mass Spectrometry (LC-MS) (Kaplan et. al. 2011). Ascarosides were analyzed by thermo spray LC-MS using a Thermo Finnigan LCQ Deca XP Max equipped with a polymer column PLRP-S (Varian, Inc) in the positive and negative ion mode (sheath gas flow 20 au, aux gas 5 au, spray voltage 5 kV and transfer line temperature of 280° C.). Ten or 20 µl of samples were injected on a 5 µM PLRP-S column using a column oven temperature of 60° C. and a flow rate of 1.0 ml/min with a gradient of solvent A (0.1% formic acid water) and solvent B (90% acetonitrile with 10 mM ammonium formate) from 90% solvent A and 10% solvent B for 2 min followed by a linear gradient to 95% B in 18 min and a 5 min return to the starting composition. Separate analyses were performed to quantify ascr#1, ascr#3 and ascr#8 content in negative ion mode and ascr#2, ascr#4 and ascr#7 in positive ion mode. Standard curves were prepared for all ascarosides using synthetic compounds prior to analyses and control samples were analyzed before and after liquid culture samples. Four ascarosides were common to all three liquid media. The concentrations of each were measured from the liquid cultures that produced 60% dauers.

Example 3

Beneficial Effects of EPN Dispersant Utilization in Field Application of Nematodes as Biocontrol Agents It is anticipated that by using the composition and method according to this invention, the efficacy of nematode biocontrol on preventing plant damage will be increased by between at least about 1-100%, e.g. by 1%, by 2%, by 5%, by 10%, by 20% by, 30%, by 40%, by 50%, by 60%, by 70%, by 80%, by 90%, by 100%.

In certain embodiments, it is estimated that the pheromone extract treatment increases efficacy of nematodes as a biocontrol between 40% and 60%. The increase is 40-60% in insect mortality.

Example 4

Conditions for Growing Nematodes to Produce EPN Disperant Composition

Growing nematodes in insects is considered as in vivo growth, growing nematodes outside the insect just with its symbiotic bacteria in liquid or solid media is considered as in vitro growth.

*Steinernema* or *Heterorhabditis* spp. (*Steinernema carpocapsae, Steinernema feltiae, Steinernema kraussei, Steinernema glaseri, Steinernema scapterisci, Steinernema riobrave, Steinernema kushidai, Steinernema scarabaei* or *Heterorhabditis bacteriophora, Heterorhabditis megidis, Heterorhabditis indica, Heterorhabditis marelatus, Heterorhabditis zealandica, Heterorhabditis downesi, Heterorhabditis marelata*) are grown on *Galleria mellonella* larvae (wax worms, wax moth). The ratio of nematodes is 25-200 IJs per wax worm larvae. Other insect hosts can be used such as *Tenebrio molitor* (meal worms) larvae navel orangeworm (*Ameylois transitella*), tobacco budworm (*Heliothis virescens*), cabbage looper (*Trichoplusia ni*), pink bollworm (*Pectinophora gossypiella*), beet armyworm (*Spodoptera exigua*), corn earworm (*Helicoverpa zea*), gypsy moth (*Lymantria dispar*), house cricket (*Acheta domesticus*) and various beetles (Coleoptera). After two days, the infected larvae are placed into new 6 cm diameter petri dishes and the white trap method is used to collect IJs. It takes about 7-10 days from infection to emergence of IJs. Once IJs form and leave the cadavers (or 3 days after emergence of the IJs), cadavers are collected to extract pheromones.

An average commercial package of nematodes contains 5 million IJs. To treat such a package, pheromones need to be extracted from about 100-200 insect larvae infected with nematodes. The extract from 100 insect host cadavers is diluted in 20-60 ml of water and the extract from 200 insect host cadavers is diluted in 40-120 ml of water where a package of IJs is placed for 20 min for activation.

Alternatively, nematode IJs are introduced to a pure culture of their symbiont in a nutritive medium at optimum growth temperature in a solid agar medium or a liquid culture with aeration in shake flasks, stirred bioreactors, airlift bioreactors (Shapiro et. al. 2012, Inman III et. al., 2012). Media for in vitro approaches is preferably animal product based (e.g., pork kidney or chicken offal) or includes various ingredients such as peptone, yeast extract, eggs, soy flour, and lard. Exemplary in vitro medium recipes for solid or liquid fermentation are disclosed, for example, in McMullen II and Stock, 2014.

In vitro growth recipes are the same for both liquid and solid medium except for the agar. The liquid medium does not contain agar, solid medium does because agar is the solidifying agent.

For Liver-kidney Agar (for 500 ml): Beef liver (50 g), Beef kidney (50 g), Sodium chloride 2.5 g (0.5% final concentration), Agar, 7.5 g (1.5% agar, final concentration), 500 ml distilled $H_2O$.

For Lipid Agar (for 1 L): Nutrient broth (8 g), Yeast extract (5 g), Magnesium chloride hexahydrate 10 ml (0.2 g/ml), Corn oil, 4 ml, Corn syrup, 96 ml combine 7 ml corn syrup in 89 ml heated $H_2O$ and swirl for homogeneity, Agar (15 g), Distilled $H_2O$ (890 ml). Nematode IJs are inoculated into liquid medium with a density between about 300-4,000 nematodes per ml at 25 or 28 degrees centigrade until nematodes reproduce and form IJs again (about 20-60% newly formed IJs). Such cultures may be synchronized cultures or unsynchronized cultures. Once new IJs are formed in the liquid cultures, nematodes are separated from the liquid medium. Then medium is centrifuged to remove the bacteria. The supernatant is frozen and lyophilized. The dry medium is extracted with alcohol and dried. Then it is extracted with water and dried. If the starting volume of the medium is 1 L, the dry extract is diluted with 1 L and can be diluted up to 3 L of water. A package of commercially available nematodes (3-5 million IJs) is treated with about 100 ml of the extract.

See, for example, Inman III, F. L., Singh, S., Holmes, L. D. (2012) Mass Production of the Beneficial Nematode *Heterorhabditis bacteriophora* and Its Bacterial Symbiont *Photorhabdus luminescens*. Indian J Microbial. 52: 316-324; McMullen II, J. G., Stock S. P. (2014). In vivo and In vitro Rearing of Entomopathogenic Nematodes (Steinernematidae and Heterorhabditidae). J. Vis. Exp. (91), e52096, doi:10.3791/52096; Shapiro-Ilan, D. I., Han, R., Dolinksi, C. (2012). Entomopathogenic Nematode Production and Application Technology. J Nematol. 44(2): 206-217.

7.0 REFERENCES

Choe A, Sternberg P W, Schroeder F C, von Reuss S H, Kaplan F, Teal P E A, Alborn H T (2012) Small molecule compounds that control plant and insect pathogenic nematodes. Patent Application No. 61/620,331.

Kaplan F, Alborn H T, von Reuss S H, Ajredini R, Ali J G, Akyazi F, Stelinski L L, Edison A S, Schroeder F C, Teal P A E (2012) Interspecific nematode signals regulate dispersal behavior. *PLoS ONE* 7: e38735

Kaplan F, Srinivasan J, Mahanti P, Ajredini R, Durak O, Nimalendran R, Sternberg P W, Teal P E A, Schroeder F C, Edison A S and Alborn H T (2011) Ascaroside expression in *Caenorhabditis elegans* is strongly dependent on diet and developmental stage. *PLoS ONE* 6: e17804.

Srinivasan J, Kaplan F (Co-first, Project leader), Ajredini R, Zachariah C, Alborn H, Teal P, Malik R U, Edison A, Sternberg P W, and Schroeder F C (2008) A synergistic blend of small molecules differentially regulates both mating behavior and development in *Caenorhabditis elegans*. Nature 454: 1115-1118.

What is claimed is:

1. A method for obtaining a nematode dispersal inducing composition comprising:

a. Obtaining a nutrient depleted nematode growth medium selected from the group consisting of liquid broth, agar medium, and insect host cadaver, depleted of nutrients by growing said nematodes to stasis in said growth medium;

b. Producing an alcohol-growth medium mixture by adding an alcohol to said growth medium to achieve a final concentration of between about 10% to about 95% of said alcohol in said growth medium;

c. Centrifuging said alcohol-growth medium mixture to remove solid or insoluble matter while maintaining a supernatant from said centrifuging;

d. Drying the supernatant from said centrifuging to produce a dry extract;

e. Resuspending said dry extract in an aqueous medium to produce a water-soluble pheromone extract;

f. Centrifuging said water-soluble pheromone extract to remove water-insoluble compounds while maintaining a water soluble supernatant; and g. Freeze drying said water-soluble supernatant to produce a dry nematode dispersal composition.

2. The method according to claim 1 wherein said alcohol is selected from the group consisting of ethanol, methanol and mixtures thereof.

3. The method according to claim 1 wherein said growth medium is selected from the group consisting of a growth medium in which non-pathogenic bacterivore nematodes or insect or entomopathogenic nematodes have been grown.

4. A nematode dispersal inducing composition produced by a method for obtaining said nematode dispersal inducing composition comprising:

a. Obtaining a nutrient depleted nematode growth medium selected from the group consisting of liquid broth, agar medium, and insect host cadaver, depleted of nutrients by growing said nematodes to stasis in said growth medium;

b. Producing an alcohol-growth medium mixture by adding an alcohol to said growth medium to achieve a final concentration of between about 10% to about 95% of said alcohol in said growth medium;

c. Centrifuging said alcohol-growth medium mixture to remove solid or insoluble matter while maintaining a supernatant from said centrifuging;

d. Drying the supernatant from said centrifuging to produce a dry extract;

e. Resuspending said dry extract in an aqueous medium to produce a water-soluble pheromone extract;

f. Centrifuging said water-soluble pheromone extract to remove water-insoluble compounds while maintaining a water soluble supernatant; and g. Freeze drying said water-soluble supernatant to produce a dry nematode dispersal composition.

5. A nematode dispersal composition produced by fractionating the composition according to claim 4 and, utilizing activity guided fractionation, combining fractions in different ratios to achieve a purified nematode dispersal composition which is dried.

6. A nematode dispersal composition according to claim 4 comprising an extract of a growth medium in which nematodes have been grown to a stage of nutrient depletion from which said nematodes have departed or have been removed and wherein said growth medium has been extracted and dried.

7. The nematode dispersal composition according to claim 6 wherein said composition comprises nematode pheromones.

8. The nematode dispersal composition according to claim 7 wherein said composition comprises nematode ascarosides in a concentration and ratio sufficient to induce nematode dispersal when contacted with an effective amount of said composition.

9. A method for using the composition according to claim 4 to disperse nematodes in field application of said nematodes which comprises:

a. Dissolving said composition in an aqueous medium to produce an aqueous nematode dispersal composition;

b. Mixing said aqueous nematode dispersal composition with nematodes to activate said nematodes for dispersal prior to field application of said nematodes.

10. The method according to claim 9 wherein said nematodes are maintained in contact with said aqueous nematode dispersal composition for a period of at least about 15-30 mins prior to field application of said nematodes.

11. The method according to claim 10 wherein said nematodes are filtered prior to field application.

* * * * *